United States Patent
Epstein

(10) Patent No.: US 10,111,621 B2
(45) Date of Patent: Oct. 30, 2018

(54) DISPOSABLE PRINTED CONDUCTIVE LEAD ELEMENTS FOR MEDICAL APPLICATIONS

(71) Applicant: Core Medical Concepts LLC, Hatboro, PA (US)

(72) Inventor: Stephen T. Epstein, Hatboro, PA (US)

(73) Assignee: Nikohed USA Inc., Hatboro, PA (US)

( * ) Notice: Subject to any disclaimer, the term of this patent is extended or adjusted under 35 U.S.C. 154(b) by 241 days.

(21) Appl. No.: 14/789,900

(22) Filed: Jul. 1, 2015

(65) Prior Publication Data

US 2016/0000347 A1    Jan. 7, 2016

Related U.S. Application Data

(60) Provisional application No. 62/019,458, filed on Jul. 1, 2014.

(51) Int. Cl.
  *A61B 5/00*    (2006.01)
  *A61B 5/0416*    (2006.01)

(52) U.S. Cl.
  CPC .......... *A61B 5/6832* (2013.01); *A61B 5/0416* (2013.01); *A61B 2562/12* (2013.01); *A61B 2562/222* (2013.01); *Y10T 428/24802* (2015.01); *Y10T 428/24942* (2015.01); *Y10T 428/26* (2015.01); *Y10T 428/266* (2015.01); *Y10T 428/2839* (2015.01)

(58) Field of Classification Search
  CPC ..... Y10T 428/24802; Y10T 428/24942; Y10T 428/26; Y10T 428/266; Y10T 428/2839
  See application file for complete search history.

(56) References Cited

U.S. PATENT DOCUMENTS

| | | | |
|---|---|---|---|
| 6,006,125 A | 12/1999 | Kelly et al. | |
| 2004/0210149 A1* | 10/2004 | Wenger | A61B 5/6841 600/509 |
| 2007/0285868 A1* | 12/2007 | Lindberg | A61B 5/0245 600/382 |
| 2009/0069658 A1* | 3/2009 | Say | A61M 5/1723 600/347 |

* cited by examiner

*Primary Examiner* — Betelhem Shewareged
(74) *Attorney, Agent, or Firm* — LaMorte & Associates, P.C.

(57) ABSTRACT

A conductive lead that connects a medical sensor or probe to a monitoring or analytical machine. The conductive lead is flexible, lightweight and can be manufactured at a very low cost. The conductive lead has a dielectric flexible substrate. Conductive ink is printed upon the flexible substrate. The conductive ink forms contact pads and connection lines on the flexible substrate. The connection lines electrically interconnect the various conductive pads. An insulation layer covers the connection lines The insulation layer can be dialectic ink that is printed atop the conductive ink. Peel-away protective covers are used to cover the contact pads. Any one of the contact pads can be exposed for use by removing the protective cover that covers it. The contact pads are used to electrically interconnect with both the sensor and the machine.

12 Claims, 10 Drawing Sheets

DISPOSABLE PRINTED CONDUCTIVE LEAD ELEMENTS FOR MEDICAL APPLICATIONS

RELATED APPLICATIONS

This application claims the benefit of provisional patent application No. 62/019,458 filed Jul. 1, 2014.

BACKGROUND OF THE INVENTION

1. Field of the Invention

In general, the present invention relates to the structure of conductive lead elements that interconnect probes and sensors to medical analysis equipment. The present invention also relates to methods of forming conductive lead elements using printed conductive ink.

2. Prior Art Description

Many medical testing and monitoring systems require that various probes and sensors be attached to the body of a patient. For example, to monitor blood oxygen levels, a pulse oximeter is commonly applied to the tip of the finger. To perform an electrocardiogram, several sensors are attached to the torso and limbs. In each case, the sensor or probe is attached to medical equipment using wire leads. This presents multiple problems.

The primary problem with the wire leads is one of expense. Traditional wire leads contain copper wire, which is expensive. Furthermore, many wire leads have complex structures. For instance, the wire leads that interconnect with a pulse oximeter contains two sets of copper wires that are each shrouded in a conductive sheath to prevent signal interference. The complexity of the wire lead adds significantly to its expense. However, many hospitals routinely use wire leads for only one patient and throw the wire lead away each time a patient is discharged. The replacement costs associated with replacing wire leads costs hospitals, clinics and physicians' offices millions of dollars each year.

The wiring leads for medical equipment, such as electrocardiograms, are so extensive and complex, that they are rarely replaced. Rather, many hospitals, clinics and physicians' offices use disposable probes and repeatedly connect to those probes using the same wiring harnesses. This, of course, presents problems with patient-to-patient contamination. Wiring harnesses come into contact with a patient's skin and clothing. As such, they can be contaminated with bacteria, viruses, blood and/or other bodily fluids.

As a consequence, healthcare providers are required to balance the risks and costs associated with replacing or reusing wire leads. Healthcare providers must either absorb the large expense of replacing or sterilizing wire leads after each use, or they must assume the dangers and complications of potentially cross-contaminating patients by reusing wire leads.

In the prior art, attempts have been made to replace expensive wire leads with less expensive elements, such as printed flexible substrates. Such prior art is exemplified by U.S. Pat. No. 6,006,125 to Kelly, entitled "Universal Electrocardiogram Sensor Positioning Device And Method". The problems associated with such printed substrates, it that they are printed in one size in the hope that one size fits all. This is clearly not true. An infant is obviously very different in size than a 200 pound man. As such, the premanufactured wiring leads must be produced in a wide variety of sizes and styles to accommodate people of different ages, sizes, shapes and genders. This requires preprinted substrates of many different sizes and lengths to be held in the inventory of a hospital or clinic. The consequence is that large sums of money must be spent on inventory. This negates the cost savings of not using traditional lead wires.

A need therefore exists for new lead elements for medical equipment that can be universally used on all patients, regardless of size, shape, age or gender. A need also exists for such lead elements that are highly reliable, yet inexpensive enough to be replaced after every use. Lastly, a need exists for new lead elements that can be manufactured at a price that is far less expensive than the cost of traditional wire leads or the cost of sanitizing traditional wire leads. These needs are met by the present invention as described and claimed below.

SUMMARY OF THE INVENTION

The present invention is a conductive lead that connects a medical sensor or probe to a monitoring or analytical machine. The conductive lead is flexible, lightweight and can be manufactured at a very low cost. As such, the conductive lead can be considered disposable since it would be cheaper to replace the conductive lead than to sterilize and reuse the conductive lead.

The conductive lead has a dielectric flexible substrate, which is a thin plastic film. Conductive ink is printed upon the flexible substrate. A primer may be used to increase the adherence between the conductive ink and the flexible substrate. The conductive ink forms contact pads and connection lines on the flexible substrate. The connection lines electrically interconnect the various conductive pads.

An insulation layer covers the connection lines so that the connection lines are interposed between the flexible substrate and the insulation layer. The insulation layer can be dialectic ink that is printed atop the conductive ink.

Peel-away protective covers are used to cover the contact pads. Any one of the contact pads can be exposed for use by removing the protective cover that covers it. The contact pads are used to electrically interconnect with both the sensor and the machine.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention system and method can be embodied in many ways, only a few exemplary embodiments are shown. These embodiments are selected in order to set forth some of the best modes contemplated for the invention. The illustrated embodiments, however, are merely exemplary and should not be considered a limitation when interpreting the scope of the claims.

Figure 1:
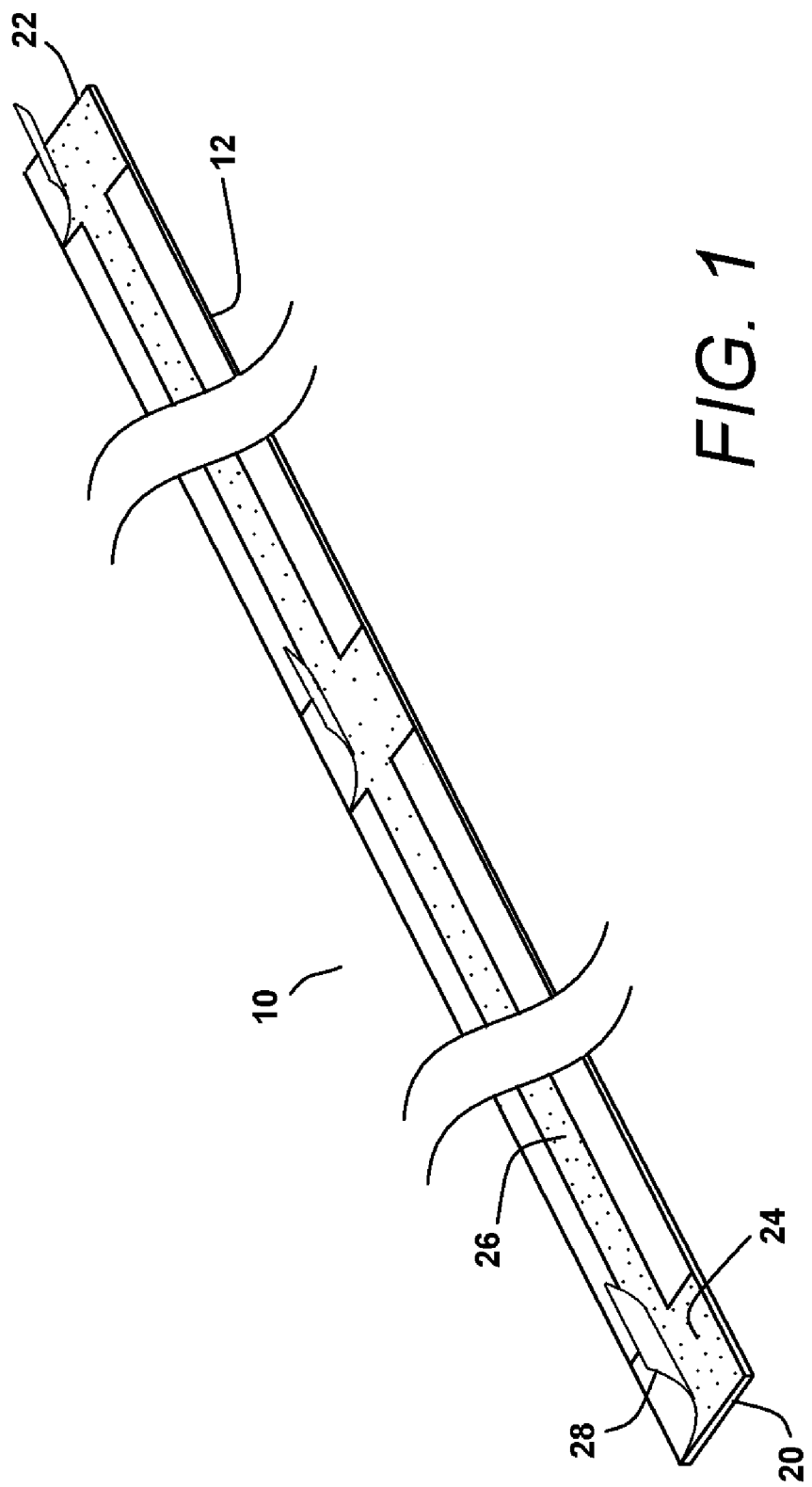
FIG. 1 is a perspective view of an exemplary embodiment of a conductive lead.
Figure 2:
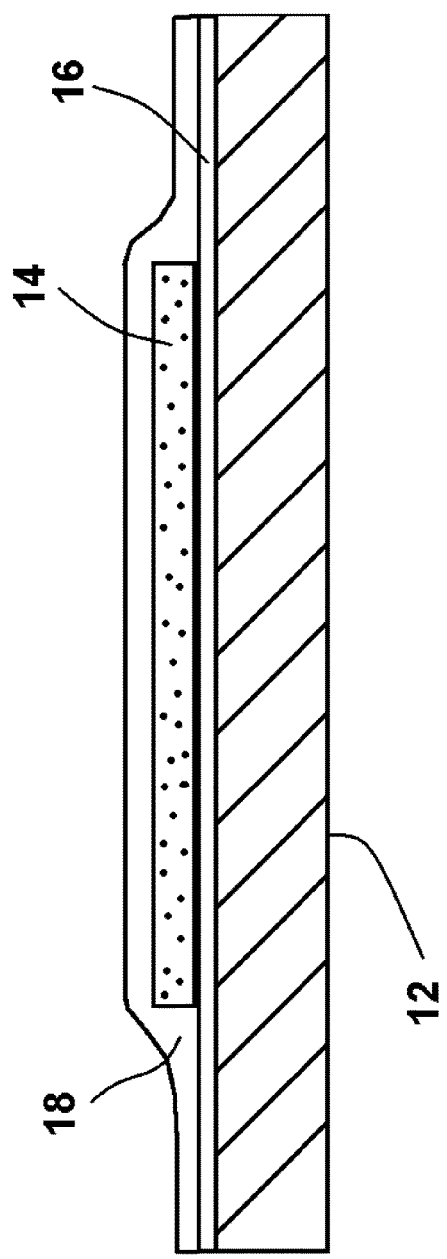
FIG. 2 is a cross-sectional view of the conductive lead shown in FIG. 1.

Referring to FIG. 1 in conjunction with FIG. 2, a conductive lead 10 is show. The conductive lead 10 has a length L1, which is preferably between eight inches and thirty-six inches. The conductive lead 10 is manufactured upon a thin flexible substrate 12 that has a preferred thickness of between 5 mil and 20 mils, so as to be highly flexible. The preferred substrate is a film of polyethylene terephthalate (PET). However, films of flashspun non-woven high-density polyethylene fiber, such as Tyvek®, can also be used. These films are dielectric, highly flexible, and resist tearing in tension.

A conductive ink 14 is printed upon the flexible substrate 12. The conductive ink 14 is preferably applied using an industrial grade electronic printer. However, alternate printing methods, such as silk-screening can also be used. Many conductive inks can be used in the printing. However, to limit distortion cracking of the ink, silver-based inks are preferred.

Depending upon the composition of the flexible substrate 12 and the composition of the conductive ink 14, the flexible substrate 12 may be coated with an aqueous primer 16 that increases the adhesion between the conductive ink 14 and the flexible substrate 12. There are many primers commercially available that are used to print ink onto PET or high-density polyethylene fiber. Many of these primers work with silver-based conductive inks and can be incorporated into the present invention. The primer 16 prevents the conductive ink 14 from peeling away from the flexible substrate 12 if the flexible substrate 12 is severely deformed during processing and/or use. The primer 16 also is beneficial in the adhesion of an insulation layer 18 over the flexible substrate 12 and conductive ink 14.

A dielectric insulation layer 18 is applied over both the conductive ink 14 and the flexible substrate 12. The dielectric insulation layer 18 can be applied in one of two ways. The dielectric layer 18 can simply be a layer of dielectric ink that is printed over the conductive ink 14 and the exposed flexible substrate 12. The dielectric ink encapsulates the conductive ink 14 so that the conductive ink 14 is interposed between the flexible substrate 12 and the dielectric ink. Alternatively, the dielectric insulation layer 18 can be a curable dielectric polymer that is sprayed or otherwise applied over the conductive ink 14 and the exposed flexible substrate 12. In either manufacturing scenario, the conductive ink 14 is interposed between the flexible substrate 12 and the dielectric insulation layer 18. Accordingly, the conductive ink 14 cannot short against the skin or any metallic object that it may inadvertently contact.

As is shown in FIG. 1, the conductive lead 10 extends between a first end 20 and an opposite second end 22. Enlarged contact pads 24 are disposed both at the first end 20 and the second end 22. The enlarged contact pads 24 are large areas of conductive ink 14 that are interconnected by a narrower line 26 of conductive ink 14. The contact pads 24 preferably have a width that is at least twice as wide as the line 26 of conductive ink 14.

During manufacture, the contact pads 24 are also coated with the dielectric insulation layer 18, as are all exposed surfaces of the conductive lead 10. However, prior to the application of the dielectric insulation layer 18, the contact pads 24 are sheltered under a peel-away protective cover 28. The peel-away protective cover 28 can be a film that is applied over the contact pads 24. However, it is preferred that the peel-way protective covers 28 be a printed layer of dielectric material that is printed onto the contact pads 24, but are selected from a material that does not adhere to the material of the contact pads 24. For example, if the contact pads 24 are printed in a conductive silver ink, the peel-away protective cover 28 can be a layer of silicone or a layer of latex printed onto the silver ink. Such material will not bond to the silver ink and will be able to peel away from the silver ink.

The contact pads 24 are present at both ends of the conductive lead 10. However, additional contact pads 24 can be periodically positioned along the length of the conductive lead 10 between its two ends 20, 22. Each of the contact pads 24 has a peel-way protective cover 28. This enables a healthcare professional to electrically interconnect to the conductive lead 10 at multiple points along its length.

Figure 3:
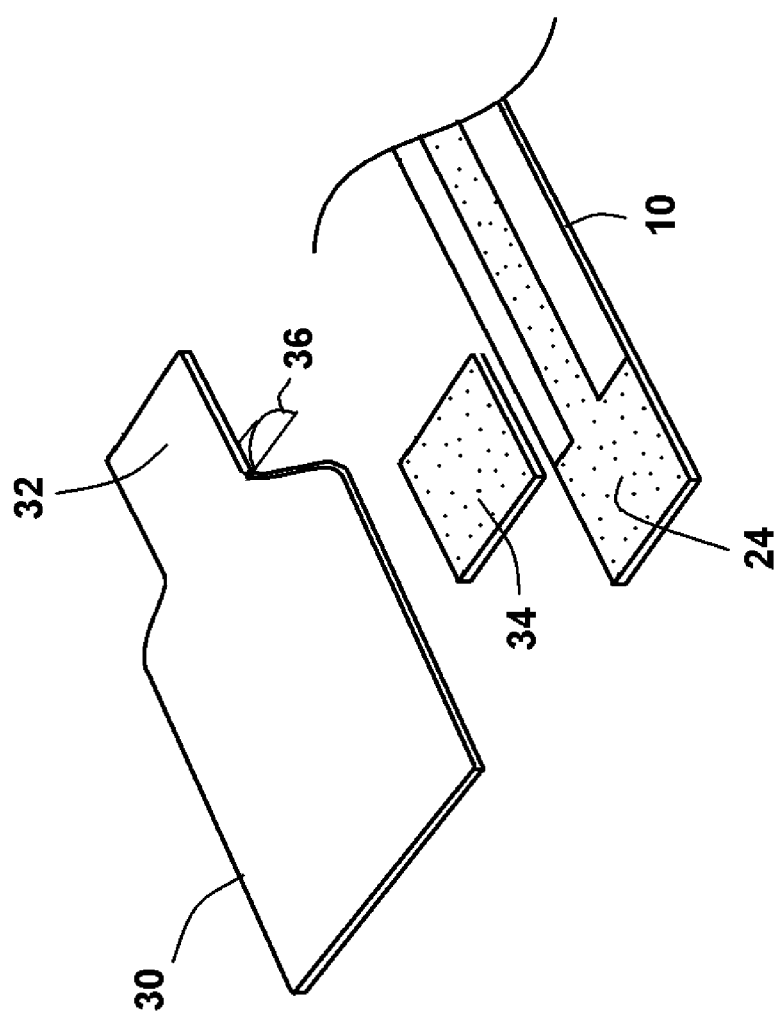
FIG. 3 shows a first type of medical sensor engaging a contact pad on the conductive lead.

Referring to FIG. 3, it will be understood that the purpose of the conductive lead 10 is to electrically interconnect with a probe or sensor 30. In the shown illustration, the sensor 30 is an ECG pad. The ECG pad is manufactured with a conductive flap 32. The conductive flap 32 is coated with a conductive adhesive 34 and is protected by a peel-way cover 36. The conductive flap 32 is exposed by removing the peel-way cover 28. The conductive pad 24 on the conductive lead 10 is likewise exposed by removing its peel-away cover 36. The conductive flap 32 is then pressed against the contact pad 24, wherein electrical continuity is achieved between the sensor 30 and the conductive lead 10.

Figure 4:
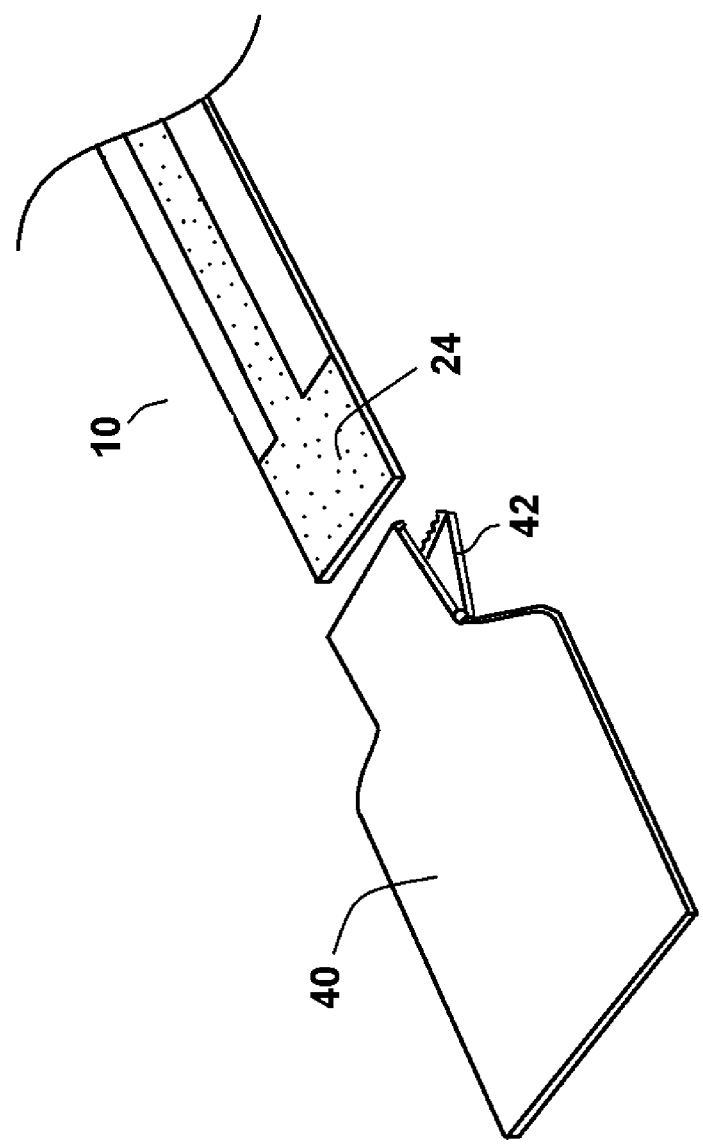
FIG. 4 shows a second type of sensor engaging a contact pad on the conductive lead.

Referring to FIG. 4, a sensor 40 is shown with an alternate connection scheme. In the embodiment of FIG. 4, the sensor 40 is provided with a conductive clip 42. The conductive clip 42 closes over the contact pad 24, therein creating electrical continuity between the sensor 40 and the conductive lead 10.

Figure 5:
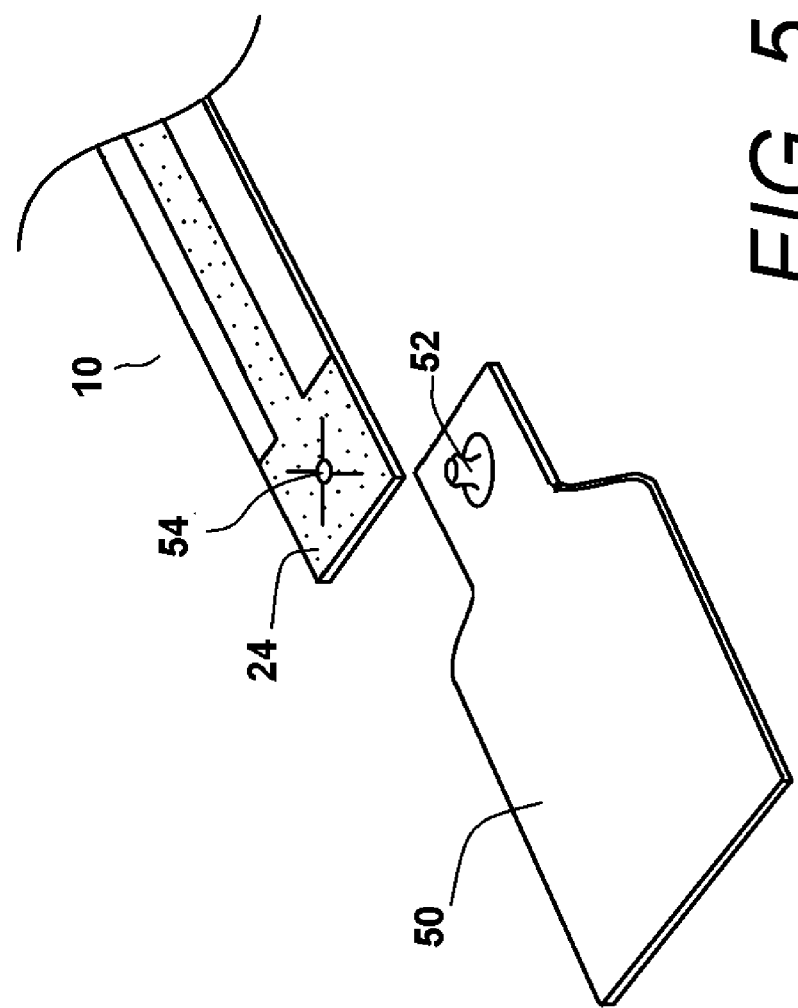
FIG. 5 shows a third type of sensor engaging a contact pad on a modified conductive lead.

Referring to FIG. 5, a sensor 50 is shown that has a nub 52 for a snap connector. Such sensors are widely used in the marketplace. In this embodiment, a slotted hole 54 can be formed through the contact pad 24 of the conductive lead 10. The slotted hole 54 passes around the nub 52, therein creating electrical continuity between the sensor 50 and the conductive lead 10.

Figure 6:
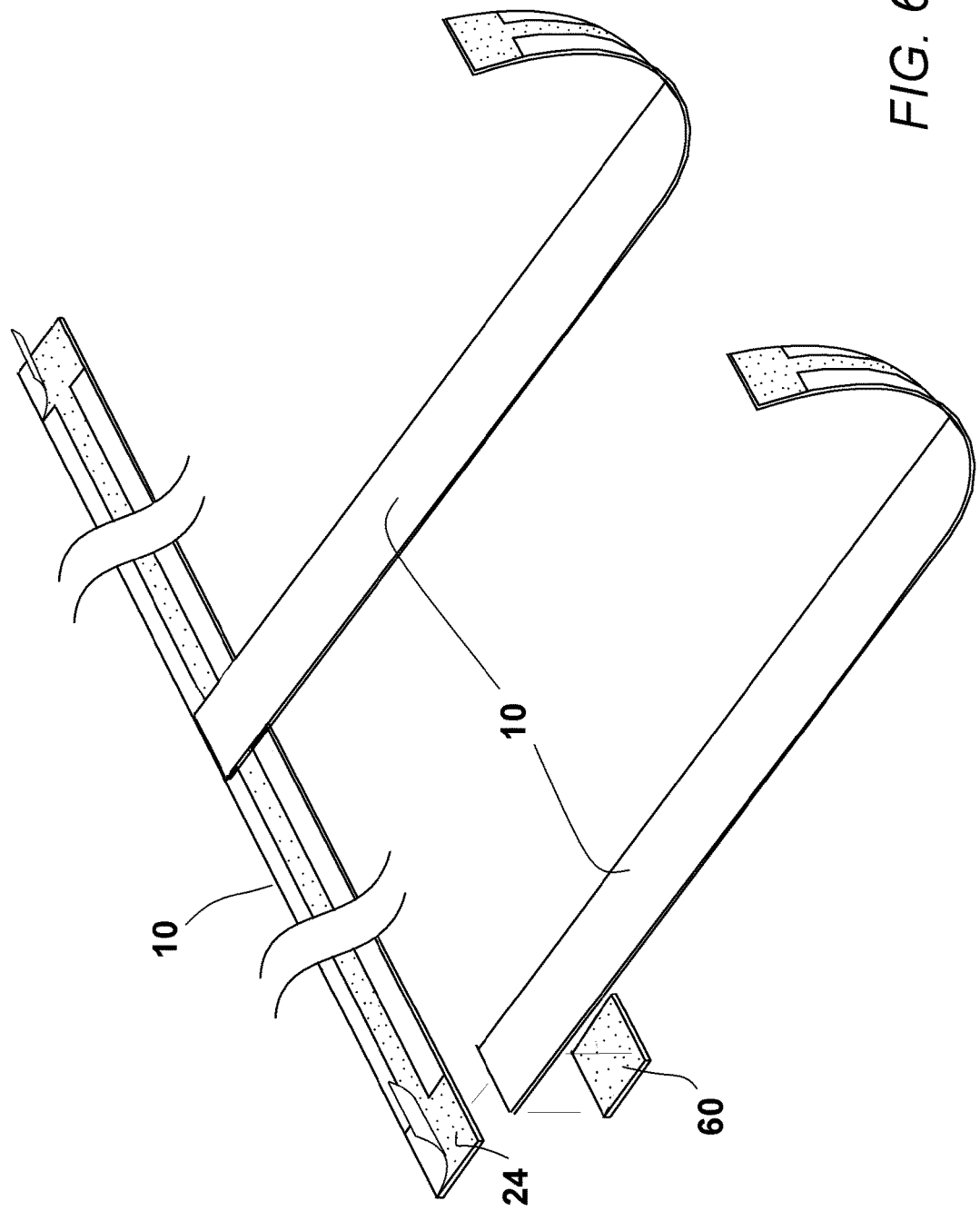
FIG. 6 shoes a plurality of conductive leads being interconnected into a harness.

Referring to FIG. 6, it can be seen that multiple conductive leads 10 can be interconnected. This is accomplished by placing a square of conductive adhesive 60 between any two contact pads 24 and pressing those contact pads 24 together. This enables conductive lead assemblies to be selectively created that have complex configurations.

Figure 7:
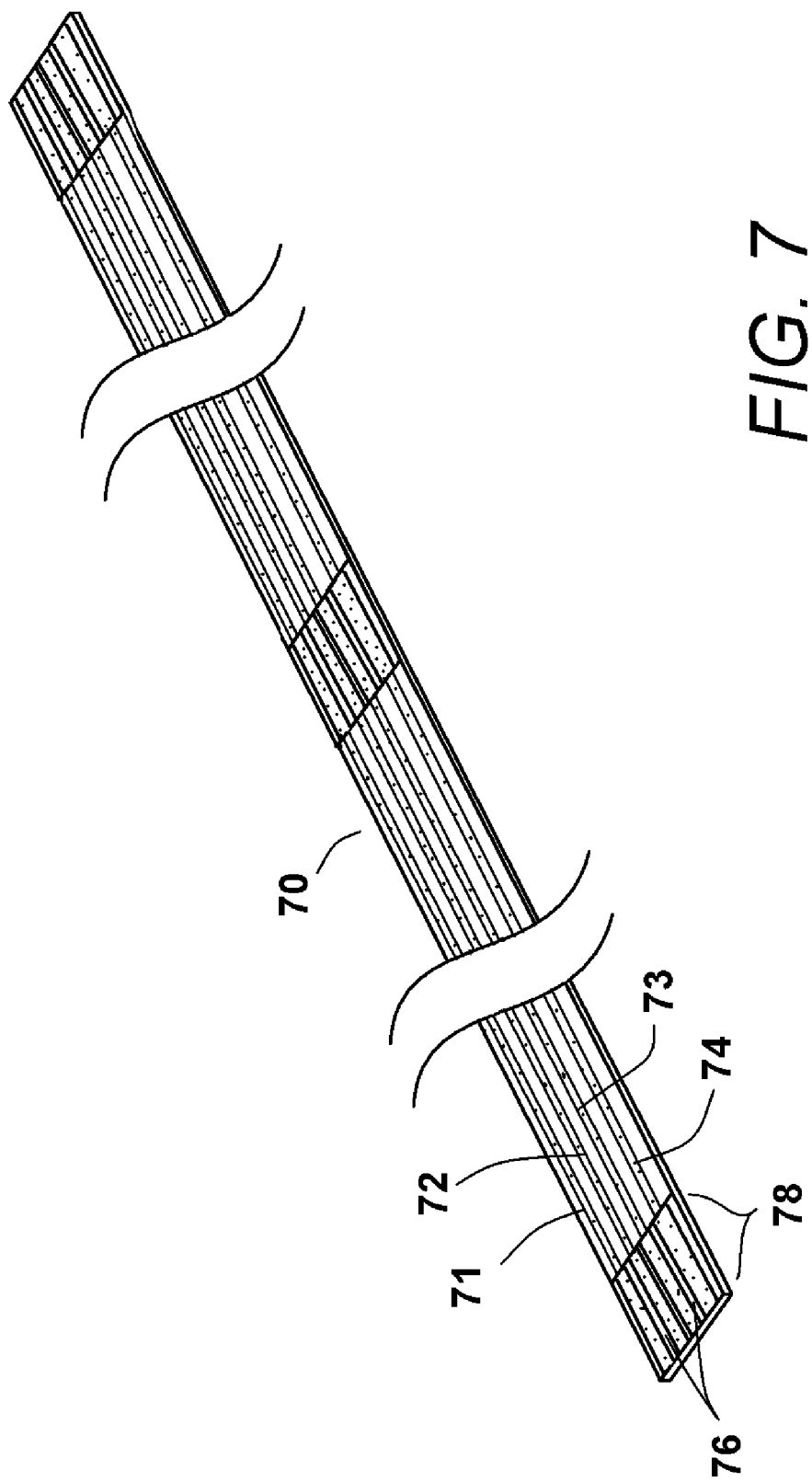
FIG. 7 shows an alternate configuration of the conductive lead for use with a four wire medical sensor.
Figure 8:
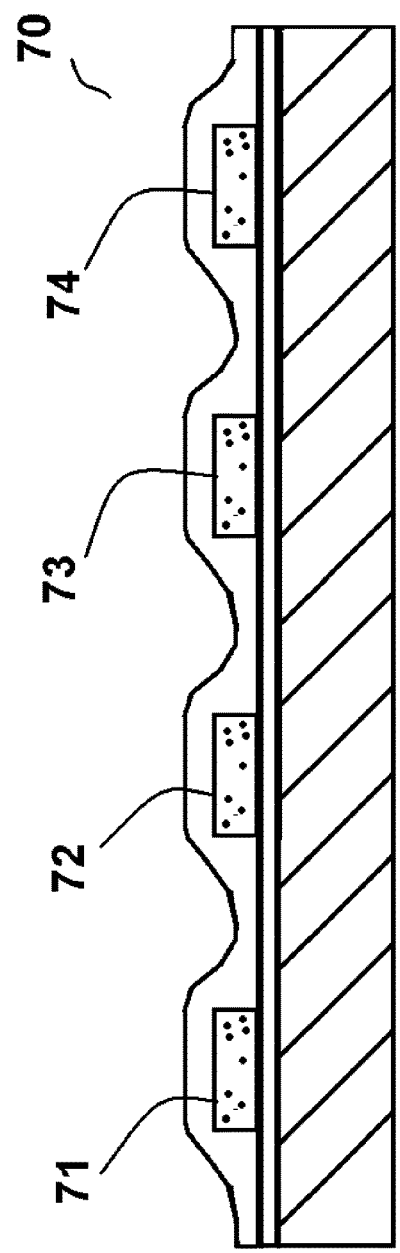
FIG. 8 is a cross-sectional view of the conductive pad shown in FIG. 7.

In the previous embodiments, each conductive lead 10 contained only a single electrical pathway from one end to the other. However, this need not be the case. Referring to FIG. 7 and FIG. 8, it can be seen that multiple conductive pathways 71, 72, 73, 74 can be printed onto one conductive lead 70. Each of the conductive pathways 71, 72, 73, 74 is isolated from the other. Each of the conductive pathways 71, 72, 73, 74 is exposed on various contact pads 76. In the shown embodiment, each of the conductive pathways has a contact pad 76 exposed in the contact pad area 78. However, this need not be the case. Each of the contact pad areas 78 may expose only one contact pad 76 that is connected to a different one of the conductive pathways 71, 72, 73, 74. In this manner, it would be very easy to connect to any one of the conductive pathways 71, 72, 73, 74.

In the shown embodiment, the conductive lead 70 contains four conductive pathways 71, 72, 73, 74. This is particularly useful for use with pulse oximeter sensors, which require four lead lines to properly operate.

Figure 9:
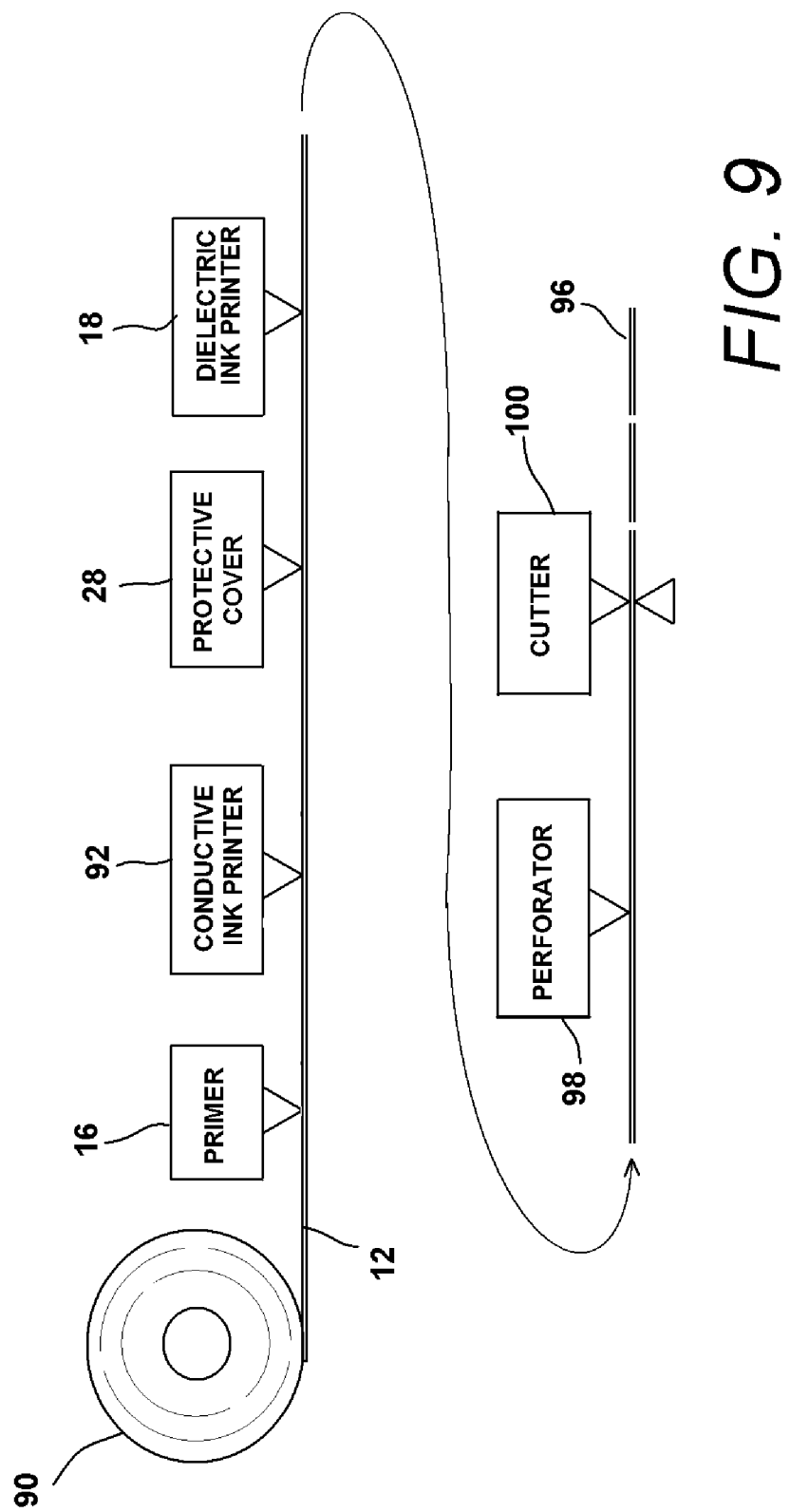
FIG. 9 is a schematic showing the production methodology used to produce the conductive leads.

In FIG. 9, a schematic is shown for producing printed conductive leads 10. Referring to FIG. 9 in conjunction with FIG. 1 and FIG. 2, it will be understood that a supply roll 90 of the flexible substrate 12 is provided. The flexible substrate 12 is coated with the primer 16. The primed substrate then advances under one or more ink printers 92. The ink printers 92 print conductive ink onto the primed substrate and produces the wide contact pads 24 and the narrow lines 26 that interconnect the contact pads 24. The conductive ink 14 may be mixed with a plasticizing agent to increase the flexibility of the ink composition. In this manner, when the flexible substrate 12 is bent, the printed conductive ink 14 does not pull away from the flexible substrate 12 or crack.

The contact pads 24 that are printed as part of the conductive leads 10 are covered with a protective cover 28. This can be done either by printing the protective cover 28 in place or applying a preformed protective cover. Once the contact pads 24 are protected, the insulation layer 18 is applied. The insulation layer 18 can be applied by printing, spraying, dipping, or by using a roller application. The insulation layer 18 is then cured.

Figure 10:
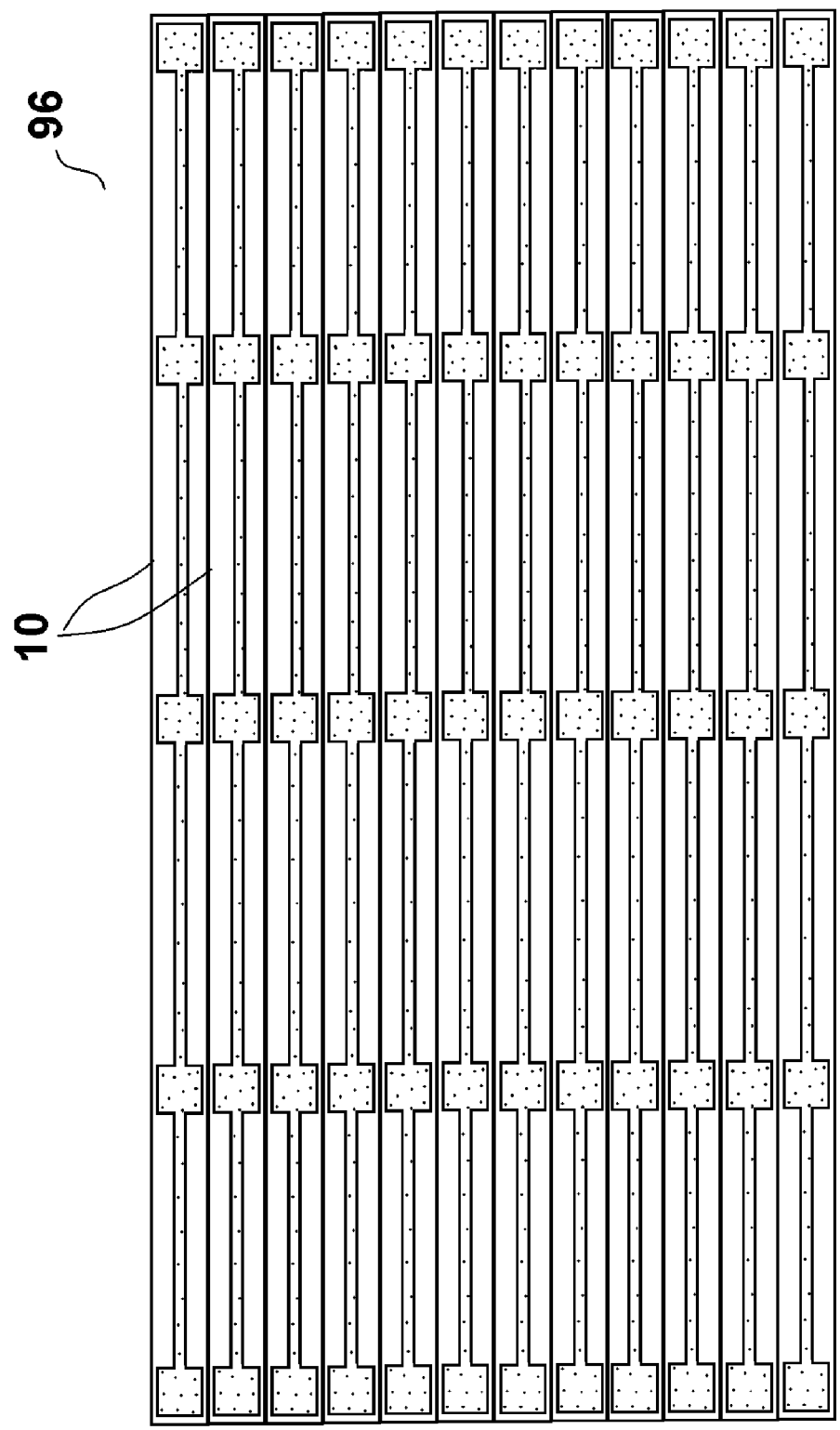
FIG. 10 shows a sheet of interconnected conductive leads.

Referring to FIG. 10 in conjunction with FIG. 9, it will be understood that the conductive leads 10 are preferably manufactured in a sheet 96, wherein multiple conductive leads 10 are produced in parallel rows to utilize as much of the flexible substrate 12 as is possible. The sheets 96 pass through a perforator 98 that perforates the sheet 96 between each of the conductive leads 10. The sheets 96 then pass through a cutter 100 that cuts the sheets to length.

To utilize the present invention, a healthcare provider is given a conductive lead 10 or a sheet 96 of conductive leads 10. If given a sheet 96, the healthcare provider pulls away the conductive leads 10 he/she needs. At one end of the conductive lead 10, the healthcare provider peels away the protective cover 28 to expose a contact pad 24. The contact pad 24 is electrically interconnected with the testing or monitoring equipment being used.

The healthcare provider can then expose any of the contact pads 24 along the length of the conductive leads. These exposed contact pads can be attached to other conductive leads or to sensors.

It will be understood that the embodiments of the present invention that are illustrated and described are merely exemplary and that a person skilled in the art can make many variations to those embodiments. All such embodiments are intended to be included within the scope of the present invention as defined by the appended claims.

What is claimed is:

1. A conductive lead for connecting a medical sensor to a machine, said conductive lead comprising:
   a dielectric flexible substrate extending a first length between a first end and a second end;
   a first contact pad printed on said dielectric flexible substrate proximate said first end;
   a second contact pad printed on said dielectric flexible substrate proximate said second end;
   a connection line that extends said first length to create a single electrical pathway from said first contact pad to said second contact pad, wherein said first contact pad, said second contact pad and said connection line are all printed from a common conductive ink;
   peel-away protective covers that cover said first contact pad and said second contact pad; and
   an insulation layer applied over said peel-way protective covers and said connection line, wherein said peel-way protective covers and said connection line are interposed between said flexible substrate and said insulation layer, wherein said first contact pad and said second contact pad can be exposed by removal of said peel-away protective covers.

2. The conductive lead according to claim 1, wherein said flexible substrate is coated with a primer and said common conductive ink is printed upon said primer.

3. The conductive lead according to claim 1, wherein said insulation layer is a printed dielectric ink.

4. The conductive lead according to claim 1, wherein said peel-away protective covers are printed atop said first contact pad and said second contact pad.

5. The conductive lead according to claim 1, wherein said flexible substrate is a plastic film having a film thickness between 5 mils and 20 mils.

6. The conductive lead according to claim 1, wherein said first contact pad and said second contact pad are at least twice as wide as said connection line.

7. The conductive lead according to claim 1, further including a sensor that connects to the human body, wherein said second contact pad electrically interconnects to said sensor.

8. The conductive lead according to claim 1, wherein said common conductive ink contains silver.

9. The conductive lead according to claim 1, further including at least one additional contact pad printed along said first length of said dielectric flexible substrate between said first end and said second end, wherein said connective line interconnects with said at least one additional contact pad.

10. A conductive lead for connecting a medical sensor to a machine, said conductive lead comprising:
    a dielectric flexible substrate extending a first length between a first end and a second end;
    a first contact pad printed on said dielectric flexible substrate proximate said first end;
    a second contact pad printed on said dielectric flexible substrate proximate said second end;
    a plurality of connection lines that extends said first length to create electrical pathways from said first contact pad to said second contact pad, wherein said first contact pad, said second contact pad and said connection lines are all printed from conductive ink;
    peel-away protective covers that cover said first contact pad and said second contact pad; and
    an insulation layer applied over said peel-way protective covers and said connection lines, wherein said peel-way protective covers and said connection lines are interposed between said flexible substrate and said insulation layer.

11. The conductive lead according to claim 10, wherein said flexible substrate is coated with a primer and said conductive ink is printed upon said primer.

12. The conductive lead according to claim 1, wherein said insulation layer is a printed dielectric ink.

* * * * *